United States Patent [19]

Pressman et al.

[11] Patent Number: 5,428,075

[45] Date of Patent: Jun. 27, 1995

[54] METHOD FOR REGENERATING A SULFONATED AROMATIC ORGANIC POLYMERIC ION-EXCHANGE RESIN BED HAVING DEACTIVATED AMINOORGANOMERCAPTAN GROUPS WITH PHENOL

[75] Inventors: Eric J. Pressman, East Greenbush; Sheldon J. Shafer, Clifton Park, both of N.Y.

[73] Assignee: General Electric Company, Schenectady, N.Y.

[21] Appl. No.: 236,815

[22] Filed: May 2, 1994

[51] Int. Cl.$^6$ .................. B01J 38/52; B01J 49/00; C07C 39/12; C07C 39/16
[52] U.S. Cl. ................................ 521/26; 210/674; 525/384; 568/727; 568/728
[58] Field of Search .......................... 521/26; 210/674; 568/727, 728

[56] References Cited

U.S. PATENT DOCUMENTS 4,051,079  9/1977  Melby ........................... 521/26

FOREIGN PATENT DOCUMENTS 1183564  11/1970  United Kingdom .

*Primary Examiner*—Fred Zitomer
*Attorney, Agent, or Firm*—William H. Pittman

[57] ABSTRACT

A method is provided for regenerating deactivated sulfonated aromatic organic ion-exchange resin beds, such as a polystyrene ion-exchange resin bed, having chemically combined amino organo mercaptan groups with anhydrous phenol at an elevated temperature.

7 Claims, No Drawings

METHOD FOR REGENERATING A SULFONATED AROMATIC ORGANIC POLYMERIC ION-EXCHANGE RESIN BED HAVING DEACTIVATED AMINOORGANOMERCAPTAN GROUPS WITH PHENOL

Reference is made to copending application Ser. No. 08/236,816 filed concurrently herewith.

BACKGROUND OF THE INVENTION

The present invention relates to an anhydrous phenol treatment method for restoring deactivated sulfonated aromatic organic polymeric ion-exchange resin having chemically combined aminoorganomercaptan groups. More particularly, a method is provided for treating a deactivated ion exchange resin with anhydrous phenol at elevated temperatures to effect the reaction of phenol with deactivated aminoorganomercaptan groups and the simultaneous elution of phenolic reaction products from the ion-exchange resin.

As shown in copending application Ser. No. 08/236,816 a sulfonated aromatic organic polymeric ion-exchange resin bed having chemically combined aminoorganomercaptan groups can be used to catalyze the condensation of phenol and ketone, such as acetone. However, excessive exposure of such "thiol containing" ion-exchange resin to phenol contaminated with at least 1 ppm of hydroxyacetone can substantially reduce the effectiveness or "deactivate" the ion-exchange resin. It has been found that contact between the hydroxyacetone contaminant and aminoorganomercaptan groups can result in the formation of a chemically combined species. The species can substantially interfere with the ability of the ion-exchange resin to perform effectively as a condensation catalyst for making bisphenol.

Another application of the thiol containing ion exchange resin taught in copending application Ser. No. 08/236,816 is as a sacrificial ion-exchange resin guard bed having chemically combined aminoorganomercaptan groups. The ion-exchange resin guard bed can be used to provide a purified phenol effluent substantially free of hydroxyacetone which can extend the life of the ion-exchange resin condensation reactor bed.

SUMMARY OF THE INVENTION

The present invention is based on the discovery that the regeneration of a deactivated ion-exchange resin can be effected with a batch or flow treatment of the resin with anhydrous phenol at elevated temperatures. It has been found that if a deactivated sulfonated aromatic organic polymeric ion-exchange resin having aminoorganomercaptan groups which have been chemically modified, is treated with substantially anhydrous phenol having 0 ppm to 100 ppm of water at a temperature of 70° C. to 120° C., a separation or elution can result of phenolic reaction products having a molecular weight in the range of about 200 to 400. Substantial regeneration of the ion-exchange resin can be established when high pressure liquid chromatography (HPLC) shows that effluent arising from the hot anhydrous phenol treatment has less than 1 ppm of a phenolic trisphenol reaction product as defined hereinafter.

STATEMENT OF THE INVENTION

A method for regenerating a deactivated sulfonated aromatic organic polymeric ion-exchange resin having chemically combined aminoorganomercaptan groups and aminoorganomercaptan groups which have been chemically modified as a result of contact with hydroxyacetone during a phenol-ketone condensation reaction comprising, treating the deactivated sulfonated aromatic organic polymeric ion-exchange resin at a temperature of 70° C. to 120° C. with anhydrous phenol having from about 0 to about 0.01% by weight of water until a phenolic reaction mixture is formed consisting essentially of a mixture of phenol and a trisphenol reaction product as a result of contact between the deactivated sulfonated aromatic organic polymeric ion-exchange resin and anhydrous phenol, where the phenolic reaction mixture has less than about 1 ppm of the trisphenol reaction product as determined by HPLC.

The principal reaction product resulting from contact between anhydrous phenol and the deactivated ion-exchange resin is a material which is isomeric with the trisphenol shown below based on mass spectral data:

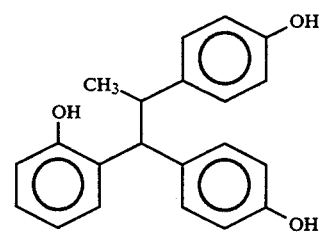

As used hereinafter, the expression "thiol containing", or "chemically combined," which is sometimes employed with reference to aminoorganomercaptan groups, means that these groups can be either ionically or covalently bound to the backbone of the sulfonated aromatic organic polymer such as a polystyrene resin. An example of an ionically bound aminoorganomercaptan groups is shown by Pressman et al. U.S. Pat. No. 4,584,416, which is incorporated herein by reference. Covalently bound aminoorganomercaptan groups is shown by Faler et al. U.S. Pat. No. 4,455,409.

Useful in the practice of the invention, is sulfonated aromatic organic polymer having ionically bound aminoorganomercaptan groups of the formula,

where R is a $C_{(2-10)}$ divalent organo radical, and $R^1$ is a monovalent radical selected from hydrogen or a $C_{(1-8)}$ alkyl radical.

There are included by the $C_{(2-10)}$ organo radicals of R of formula (1) divalent $C_{(2-10)}$ aliphatic radicals, such as dimethylene, trimethylene, tetramethylene, pentamethylene, hexamethylene; aromatic radicals, such as phenylene, xylylene, tolylene, naphthylene, etc. R also includes aliphatic and aromatic radicals as previously defined, which are further substituted with halogen radicals, for example, chloro, bromo, fluoro, etc. There are included by $R^1$ radicals of formula (1) monovalent alkyl radicals, such as methyl, ethyl, propyl, butyl, pentyl, hexyl, heptyl and octyl.

The sulfonated aromatic organic polymer which can be used in the practice of the present invention to make ion-exchange catalyst having ionically bound alkylaminoorganomercaptan groups of formula (1) include, for example, Amberlite-118, manufactured by the Rohm and Haas Company, Dowex 50WX4, manufactured by Dow Chemical Company and other sulfonated aromatic organic polymers, such as sulfonated polystyrenes which have been crosslinked with divinylbenzene.

The ion-exchange resins of the present invention can be prepared by effecting reaction between sulfonated aromatic organic polymer and N-alkylaminoorganomercaptan monomer which can be in the form of the hydrohalide or corresponding hydrotosylate. A convenient synthesis of the N-alkylaminoorganomercaptan hydrotosylate, for example, can involve an initial reaction between a bromochloroalkane and an alkali metal thiosulfate which can be refluxed in an inert atmosphere in an organic solvent, such as aqueous methanol. There can be added to the resulting reaction mixture, an appropriate alkyl amine which can be further refluxed. Methanol and excess alkyl amine can be distilled from the mixture and isopropanol added to remove the water by azeotropic distillation. The alkylaminoorganothiosulfate and by-product alkali metal halide can then be isolated free of water by filtration of the isopropanol slurry.

A mixture of the above alkylaminoorganothiosulfate and para toluenesulfonic acid monohydrate with methanol can be refluxed under nitrogen, followed by a standard organic extraction and work up which provides the desired product in a chlorinated hydrocarbon solvent. The tosylate salt can then be precipitated by addition of an appropriate aliphatic hydrocarbon solvent and isolated by filtration.

The ion-exchange resin catalyst of the present invention having ionically bound N-alkylaminoorganomercaptan groups can be made by effecting reaction between the sulfonated aromatic organic polymer and the N-alkylaminoorganomercaptan salt in the form of a halide salt or tosylate salt as described above. The sulfonated aromatic organic polymer in the form of a dry resin can be initially analyzed for sulfonic acid content by a standard neutralization technique and typically contains 22.1 millimoles of sulfonic acid groups per 4.70 grams of dry resin. An appropriate amount of the hydrohalide or hydrotosylate salt of the aminoorganomercaptan (typically 0.25 equivalents relative to sulfonic acid groups on the base resin) is heated as an aqueous solution in the presence of the base resin. The mixture can be stirred at a temperature in the range of room temperature to 70° C. for 4 hours while being slowly agitated and thereafter allowed to cool to room temperature. The resulting ion-exchange catalyst can thereafter be filtered, washed with water, and then vacuum oven dried.

The percent nitrogen in the ion-exchange catalyst can be determined using a Carlo Erba nitrogen analyzer. From this data, nitrogen milliequivalency/gram of dry catalyst can be determined which shows the fraction of total sulfonic acid sites occupied by N-alkylaminoorganomercaptan groups of formula (1). Mercaptan milliequivalency/per gram of dry catalyst can be determined using Ellman's reagent (A. Fontant and C. Toniolo, The Chemistry of the Thiol Group, S. Patai, Editor, John Wiley and Sons, Ltd., London (1979), pp. 288–290)

In order that those skilled in the art will be better able to practice the invention, the following example is given by way of illustration and not by way of limitation. All parts are by weight.

EXAMPLE

A contaminated thiol containing aromatic organic polymer was prepared by initially making a "virgin catalyst" from Amberlite 118, a product of the Rohm and Haas Company, in the form of polystyrene sulfonic acid crosslinked with 4% divinylbenzene(DVB). Amberlite 118 was treated with 2-aminoethanethiol until 20% of the acid sites were neutralized. The virgin catalyst was prepared by slow mechanical stirring for several hours under nitrogen of 7.5 parts of a solution of 1.75% aqueous aminoethanethiol hydrochloride (Aldrich Chemical Co.) which was prepared at room temperature using helium sparged water and 1 part Amberlite 118 sulfonic acid resin. The catalyst was filtered, washed well with water, and vacuum oven dried overnight (83° C.; house vacuum ~20 torr).

The thiol content of the catalyst was determined by HPLC using a benzoylated aliquot of a sample stripped from the sulfonic acid resin. A 200 mg of catalyst was weighed into a 4 dram vial. A magnetic stir bar and 3.5 mL of 1.5 M $NaOH_{aq}$ was added. After 4 minutes stirring, an excess (4 drops, ca. 90 mg) of benzoyl chloride was added. The solution was stirred for 40 minutes. Excess benzoyl chloride was quenched by addition of either 2.5 mL of a 1.5 M $NaOH_{aq}$ containing ca. 200 mg phenol or 1 mL water containing 4 drops n-propylamine. After stirring an additional 40 minutes, the solution was filtered and the resin was washed with a total of 40 mL methylene chloride and 40 mL water. The filtrate layers were separated and the aqueous layer washed with 40 mL methylene chloride. The combined organic layers were dried over $MgSO_4$ anhyd, filtered, and rotary evaporated. HPLC analysis was performed using an HP1090 liquid chromatography with 100 mm×4.6 mm 5 um Hewlett-Packard ODS Hypersil reverse phase column with monitoring at 235 nm, 254 nm and 280 nm. Injections were of 10% solutions in acetonitrile containing acetophenone as internal standard.

The virgin catalyst was deactivated in continuous BPA reaction using feed enriched with hydroxyacetone (HA) (feed=8/1 phenol/acetone mole ratio, also containing 228 ppm HA; WHSV=20 g feed*$g^{-1}$ catalyst,$hr^{-1}$; 70° C., 8 hr). The thiol content for both the virgin catalyst and the deactivated catalyst are shown in Table 1. Batch treatment of the deactivated resin in 20% aqueous phenol (80/20 phenol/water w/w/) where water was added to partially simulate the BPA reaction conditions, resulted in essentially no increase in thiol content of the resin. Batch treatment with anhydrous phenol having less than about 100 ppm of water resulted in a substantial increase in thiol content. Flow treatment with anhydrous phenol resulted in an additional increase of thiol content over the batch-anhydrous phenol treatment. The following shows the results obtained:

TABLE 1

| Catalyst | Aminoethanethiol Content In Catalysts | |
|---|---|---|
| | Additional Treatment | meq $H_2NCH_2CH_2SH$/gram |
| Virgin | — | 0.856 |
| Deactivated | — | 0.367 |
| Deactivated | Batch-aqueous phenol | 0.381 |
| Deactivated | Batch-anhydrous phenol | 0.530 |
| Deactivated | Flow-anhydrous phenol | 0.609 |

Flow treatment of deactivated catalyst with anhydrous phenol was performed by pumping anhydrous phenol contained in a glass reservoir through heated stainless steel tubing attached to a glass column containing 17.3 gram deactivated catalyst at WHSV=6.5 (upflow) and maintained at 70° C.

Batch treatments of deactivated catalyst were performed by magnetic stirring of 5 parts purified phenol, 1 part deactivated catalyst, with and without 1 part water at 70° C. for 100 hours.

An improvement in the thiol content as a result of the anhydrous phenol treatment was accompanied by the elution of phenolic reaction products having a MW of about 200 to 400; the principal component had a molecular weight of about 320 and was derived from three phenoxy units and one HA unit. The same transformation did not occur in the presence of water, hence did not occur with the use of aqueous phenol, or under reaction conditions normally present during condensation between a phenol and a carbonyl compound.

Although the above example is directed to only a few of the many variables which can be used in the practice of the present invention, it should be understood that the present invention is directed to the deactivation of a much broader variety of sulfonated aromatic organic polymeric ion-exchange resin beds having chemically combined aminoorganomercaptan groups.

What is claimed is:

1. A method for regenerating a deactivated sulfonated aromatic organic polymeric ion-exchange resin having chemically combined aminoorganomercaptan groups and aminoorganomercaptan groups which have been chemically modified as a result of contact with hydroxyacetone during a phenol-ketone condensation reaction comprising, treating the deactivated sulfonated aromatic organic polymeric ion-exchange resin at a temperature of 70° C. to 120° C. with anhydrous phenol having from about 0 to about 0.01% by weight of water until a phenolic reaction mixture is formed consisting essentially of a mixture of phenol and a trisphenol reaction product as a result of contact between the deactivated sulfonated aromatic organic polymeric ion-exchange resin and anhydrous phenol, where the phenolic reaction mixture has less than about 1 ppm of the phenolic reaction product as determined by HPLC.

2. A method in accordance with claim, 1 where the aromatic organic ion-exchange resin is sulfonated polystyrene ion exchange resin.

3. A method in accordance with claim 1, where the aminoorganomercaptan groups are ionically bound.

4. A method in accordance with claim 1, where the aminoorganomercaptan groups are covalently bound.

5. A method in accordance with claim 1, where the aromatic organic ion-exchange resin is regenerated by a flow treatment.

6. A method in accordance with claim 1, where the aromatic organic ion-exchange resin is regenerated by a batch treatment.

7. A method in accordance with claim 1, where the aminoorganomercaptan groups are 2-aminoethanethiol groups.

* * * * *